United States Patent
Verkuijl et al.

(10) Patent No.: US 9,714,399 B2
(45) Date of Patent: Jul. 25, 2017

(54) PREPARATION OF LACTYLATES DIRECTLY FROM OIL

(71) Applicant: PURAC Biochem BV, Gorinchem (NL)

(72) Inventors: Bastiaan Jeroen Victor Verkuijl, Gorinchem (NL); Symone Kok, Gorinchem (NL)

(73) Assignee: Purac Biochem BV, Gorinchem (NL)

( * ) Notice: Subject to any disclaimer, the term of this patent is extended or adjusted under 35 U.S.C. 154(b) by 0 days.

(21) Appl. No.: 14/783,283

(22) PCT Filed: Apr. 10, 2014

(86) PCT No.: PCT/EP2014/057309
§ 371 (c)(1),
(2) Date: Oct. 8, 2015

(87) PCT Pub. No.: WO2014/167069
PCT Pub. Date: Oct. 16, 2014

(65) Prior Publication Data
US 2016/0068783 A1    Mar. 10, 2016

Related U.S. Application Data

(60) Provisional application No. 61/810,738, filed on Apr. 11, 2013.

(30) Foreign Application Priority Data

Apr. 11, 2013 (EP) .................................... 13163289

(51) Int. Cl.
| | |
|---|---|
| C07C 51/00 | (2006.01) |
| C11C 3/10 | (2006.01) |
| C11C 3/00 | (2006.01) |
| A61K 8/37 | (2006.01) |
| A61K 31/23 | (2006.01) |
| A61Q 19/00 | (2006.01) |
| C07C 59/105 | (2006.01) |
| C07C 59/235 | (2006.01) |
| C07C 67/02 | (2006.01) |

(52) U.S. Cl.
CPC ................. C11C 3/10 (2013.01); A61K 8/37 (2013.01); A61K 8/375 (2013.01); A61K 31/23 (2013.01); A61Q 19/00 (2013.01); C07C 59/105 (2013.01); C07C 59/235 (2013.01); C07C 67/02 (2013.01); C11C 3/003 (2013.01); A61K 2800/5922 (2013.01)

(58) Field of Classification Search
CPC .............. C11C 3/003; C11C 3/10; A61K 8/37
USPC ........................................................ 554/124
See application file for complete search history.

(56) References Cited

U.S. PATENT DOCUMENTS

| | | | | |
|---|---|---|---|---|
| 2,733,252 | A | | 1/1956 | Baddemeyer |
| 4,146,548 | A | * | 3/1979 | Forsythe .................. C09K 3/00 554/156 |
| 5,872,268 | A | * | 2/1999 | Kasori .................... C07C 67/03 554/163 |
| 6,383,505 | B1 | * | 5/2002 | Kaiser .................... A01N 47/44 424/405 |

FOREIGN PATENT DOCUMENTS

| | | | |
|---|---|---|---|
| IT | WO 2009125367 A1 * | 10/2009 | ............. A61K 8/362 |
| WO | 2009/125367 A1 | 10/2009 | |

OTHER PUBLICATIONS

Yuyi Shen et al: "Influence of the Dissolution Rate on the Collapse and Shedding Behavior of Monostearin/Monopalmitin-rich Coated Microbubbles", Langmuir, vol. 24, No. 18, Sep. 16, 2008, pp. 10035-10040.*
Yuyi Shen et al: "Influence of the Dissolution Rate on the Collapse and Shedding Behavior of Monostearin/Monopalmitin-rich Coated Microbubbles", Langmuir, vol. 24, No. 18, Sep. 16, 2008 (Sep. 16, 2008), pp. 10035-10040, XP055077057, ISSN: 0743-7463.
International Search Report and Written Opinion dated Jun. 26, 2014, for corresponding International Application No. PCT/EP2014/057309, filed Apr. 10, 2014.

* cited by examiner

Primary Examiner — Deborah D Carr
(74) Attorney, Agent, or Firm — Peter J. Ims; Westman, Champlin & Koehler, P.A.

(57) ABSTRACT

A process includes the transesterification of a fatty acid triglyceride ester with a salt of hydroxycarboxylic acid without making use of organic solvents. The process can carried out with natural oils as starting material and produces a mixture of medium chain mono and diglycerides and medium chain esters of hydroxycarboxylic acid.

19 Claims, No Drawings

PREPARATION OF LACTYLATES DIRECTLY FROM OIL

CROSS REFERENCE TO RELATED APPLICATIONS

This Application is a Section 371 National Stage Application of International Application No. PCT/EP2014/057309, filed Apr. 10, 2014 and published as WO 2014/167069 A1 on Oct. 16, 2014, in English which claims priority to European Patent Application No. 13163289.5 filed on Apr. 11, 2013 and U.S. Provisional Patent Application 61/810,738 filed on Apr. 11, 2013.

BACKGROUND

The discussion below is merely provided for general background information and is not intended to be used as an aid in determining the scope of the claimed subject matter.

The present disclosure relates to a process for the preparation of a salt of a fatty acid ester of hydroxycarboxylic acid which comprises heating an oil, comprising a triglyceride fatty acid ester in admixture with a salt of hydroxycarboxylic acid, the product prepared by the process and the use of said product.

A lactylate refers to a compound having an acyl group from the fatty acid attached to one (monolactylates) or several lactic acid molecules (dilactylates etc) and a proton (H+) or another cation. The fatty acid moiety consists typically of a hydrocarbon chain attached to a carboxyl group at the end. The hydrocarbon chain can contain different numbers of carbon atoms, and the bonds between the carbon atoms can be saturated or unsaturated.

Lactylates are known surfactants. These surfactants are made by reacting lactic acid with fatty acid and neutralizing. Lactylates are well known in the food industry and are used in personal care applications to improve skin feel, skin softness and moisturization and reduce tackiness during wet to dry transition after product application.

Fatty acids esters can be found in natural oils. Natural oils may contain a high proportion of glycerides of lower and medium chain fatty acids. These triglycerides form a class of lipids in which three saturated or unsaturated fatty acids are bound to a glycerol backbone. Examples of such oils are coconut oil or palm oil. These natural oils are a source of glycerol and fatty acids which can be prepared by hydrolysis to liberate their fatty acids form glycerol and then separated by e.g. fractional distillation. Due to the high presence of medium sized fatty acid chains in the triglyceride of e.g. coconut oil, these triglycerides are often used in research, medicine and food products. By esterification other esters can be prepared including the esterification with lactic acid.

SUMMARY

This Summary and the Abstract herein are provided to introduce a selection of concepts in a simplified form that are further described below in the Detailed Description. This Summary and the Abstract are not intended to identify key features or essential features of the claimed subject matter, nor are they intended to be used as an aid in determining the scope of the claimed subject matter. The claimed subject matter is not limited to implementations that solve any or all disadvantages noted in the Background.

According to the present disclosure a process has been found for the preparation of a salt of a fatty acid ester of hydroxycarboxylic acid which comprises heating an oil, comprising a triglyceride fatty acid ester in admixture with a salt of hydroxycarboxylic acid and a catalyst at a temperature at or above the melting temperature of the salt of hydroxycarboxylic acid. The mixture is then subjected to ester interchange. The temperature usually will be between 150 and 220° C.

The chemical reaction is exemplified in Formula 1

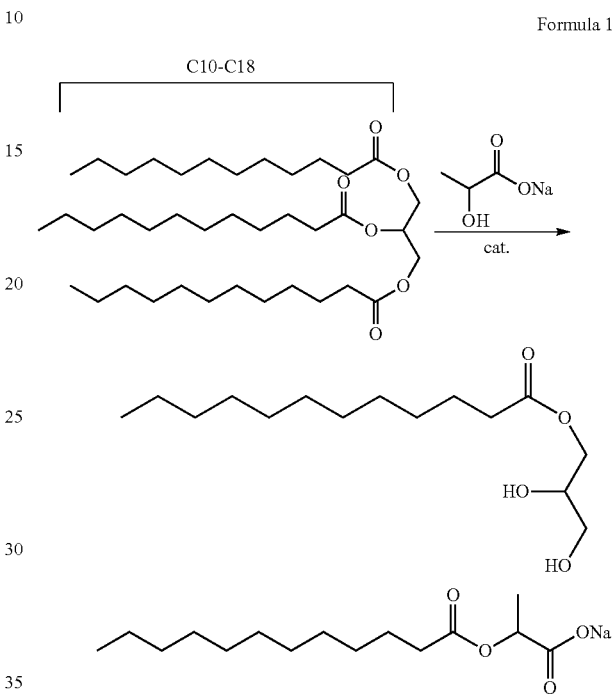

Formula 1

In Formula 1 a triglyceride from a natural oil is used as a substrate to react with anhydrous sodium lactate. Glycerol is not removed from the reaction mixture and as a result an equilibrium is formed. The resulting product is comprised of a mixture of mono and diglycerides, lactylates, lactates and glycerol (not all shown in Formula 1).

According to the present disclosure a process has been found which makes use of an ester interchange between a fatty acid triglyceride ester and a salt of hydrocarboxylic acid without making use of organic solvents. Surface active agents may be added but are not necessary.

The process has the advantage of the direct conversion into the salt of the required fatty acid ester of hydroxycarboxylic acid without using organic solvents. In addition to the hydroxycarboxylic acid ester having the above mentioned advantageous properties, the resulting mixture also comprises mono and diglyceride esters which are also known to be useful as surface acting agent and antimicrobial agent and are used in food applications and personal care applications. For such uses, the components need not to be separated but can be used directly as a mixture.

DETAILED DESCRIPTION

Hereinafter, the present disclosure is further described in detail.

The type of hydroxycarboxylic acid salt used according to the present invention can be any type of hydroxycarboxylic acid salt inasfar as it can form a liquid mixture or dispersion with the triglyceride ester. Thereto, hydrocarboxylic acid as used herein means a mono or di carboxylic acid molecule having 2-6 carbon atoms and 1-3 hydroxyl groups. Examples are lactic acid, malic acid and tartaric acid. With the term hydroxycarboxylic acid salt is, in addition to the regular salts of hydroxycarboxylic acid, also meant a cyclic carboxylic acid. Preferred are metal salts, in particular alkaline metal salts or alkaline earth metal salts. The preferred hydroxycarboxylic acid is lactic acid. Most preferred are sodium or potassium lactate or magnesium or zinc lactate. Even more preferred are sodium or potassium lactate. The preferred cyclic hydroxycarboxylic acid is lactide.

The fatty acids of the triglyceride include saturated or unsaturated fatty acids and usually have a chain with 8-24 carbon atoms. The fatty acid chain on each of the three potential ester bonds in a triglyceride ester molecule need not be the same.

In a preferred embodiment the triglyceride ester comprises C10-C18 fatty acid chains, more preferably C12-C18 fatty acid chains, even more preferably C12-C16 fatty acid chains. In another embodiment the oil in the esterification reaction is a natural oil.

The natural oil comprising the fatty acid triglyceride esters may be (partially) purified. Purification methods are well known in the art. Refined batches are commercially available and might contain close to 100% fatty acids triglyceride acids.

The natural oil used as source in the esterification reaction according to the present disclosure is usually extracted from a plant and is also called vegetable oil. Vegetable oils are often liquid at room temperature. Although many plant parts may yield oils, in commercial practice, oil is primarily extracted from seeds. Examples of natural (vegetable) oils are coconut oil, palm kernel oil, sunflower oil, palm oil, soybean oil etc.

The fatty acid composition in each of these oils is different. Coconut oil and palm kernel oil have a high amount of C12 and C14 acyl chains, sunflower oil and soybean oil are high in C18 chains whereas, e.g. palm oil has a large amount of C16 and C18 chains.

Preferred natural oils are those with a high amount of triglyceride esters with acyl groups of 12-18 carbon atoms (C12-C18). More preferred are natural oils with a high triglyceride esters with a high content of 12-16 carbon atoms acyl chains (C12-C16). Most preferred are oils with a high acyl chain length in their triglyceride esters having 12-14 carbon atoms (C12-C14). Most preferred oils are coconut oil and palm kernel oil or mixtures thereof.

The reaction process can also be carried out with mixtures of different natural oils. Preferred are mixtures with high amounts of fatty acid acyl chains with 12, 14, 16 and/or 18 carbon atoms, more preferably of 12-14 carbon atoms.

The transesterification reaction is carried out at a temperature at or above the melting temperature of the salt of hydroxycarboxylic acid. The preferred temperature will be between 150 and 220° C., more preferably between 160 and 220° C., more preferably between 160 and 200° C., even more preferably between 180 and 200° C.

In one embodiment the salt of the hydroxycarboxylic acid is first heated with the catalyst to a temperature equal to or above the melting temperature of the hydroxycarboxylic acid salt and then the triglyceride fatty acid ester is added. Thereafter the mixture is subjected to the transesterification reaction at a temperature as indicated above. Alternatively, the catalyst can also be added in a later stage e.g. with the addition of the natural oil. The catalyst and the hydroxycarboxylic acid can also be added directly to the natural oil substrate and thereafter the mixture can be heated until the reaction temperature is reached.

As mentioned here above the process does not require the presence of an organic solvent. Added non-ionic or anionic surface active agent can be present, but may also be absent. Suitable anionic surfactants are fatty acid lactylates, sulphate surfactants and sulfonate surfactant. Suitable non-ionic surfactants are fatty acid glycerides, carboxylate surfactants and alkylpolyglycosides.

In one embodiment surfactant may be present in an amount less than 20% on a weight basis as compared to the starting materials. In another embodiment less than 10 weight % of surfactant is present. In yet another embodiment less than 1 weight % of surfactant is present. In another embodiment no added surface active agents are present.

Almost any sufficiently strong alkali catalyst can be used in the present reaction. The catalyst should be able to deprotonate the alcohol group of the hydroxycarboxylic acid. Preferably, the catalyst used in the present reaction has the general formula alkali-OR wherein R stands for H or (C1-C3)alkyl. Preferably, the alkyl group is methyl. The metal moiety of the alkali catalyst is preferably the same as the metal moiety of the salt of hydroxycarboxylic acid in the reaction. Preferably this is sodium. The amount of catalyst to be added is from 0.01 to 20 mol % based on the triglyceride ester. In case lactide is used as hydroxycarboxylic acid source a higher amount of alkali might be added to convert the lactide to lactate.

The content of salt of hydroxycarboxylic acid is from 0.5 to 25 moles per mol of the triglyceride fatty acid ester.

In a typical reaction, the salt of hydroxycarboxylic acid is mixed with the catalyst, the natural oil is added and the mixture is heated to a temperature such that the hydroxycarboxylic acid will melt. Preferably the temperature is in the range of 160-220° C. Chirally pure sodium lactate has a melting point of 161-162° C. If sodium lactate is used as the source of the hydroxycarboxylic acid salt the temperature should be preferably above this melting point range.

The reaction is carried out preferably at inert atmosphere (e.g. under $N_2$) and the reaction mixture is vigorously stirred. Water or glycerol arising through the reaction will not be removed from the reaction. A dispersed, milky type of reaction mixture will be formed quickly. The reaction will be continued under stirring conditions at the high temperature. The reaction can be monitored e.g. by TLC and/or GC. If the reaction is in equilibrium, the reaction can be stopped by cooling down the reaction mixture. Usually the reaction lasts 4-24 h, more in particular 6-16 h.

It should be emphasized that in accordance with the present invention the transesterification reaction is carried out without the presence of a solvent. After the reaction, the resulting product can be neutralized if needed with a (weak) acid or any amphoteric compound, like water or sodium bicarbonate.

In one embodiment the invention relates to a process as described here before for the preparation of a mixture comprising a C10-C18 fatty acid ester of a hydroxycarboxylic acid and a mono C10-C18 fatty acid ester of glycerol or a mixture comprising a C10-C18 fatty acid ester of a hydroxycarboxylic acid and a mono and di C10-C18 fatty acid ester of glycerol.

In another embodiment the invention relates to the mixture comprising a C10-C18 fatty acid ester of a hydroxycarboxylic acid and a mono C10-C18 fatty acid ester of glycerol or a mixture comprising a C10-C18 fatty acid ester of a hydroxycarboxylic acid and a mono and di C10-C18 fatty acid ester of glycerol.

In another embodiment the invention relates to a process as described here before for the preparation of a mixture comprising a C12-C18 fatty acid ester of a hydroxycarboxylic acid and a mono C12-C18 fatty acid ester of glycerol or a mixture comprising a C12-C18 fatty acid ester of a hydroxycarboxylic acid and a mono and di C12-C18 fatty acid ester of glycerol.

In yet another embodiment the invention relates to the mixture comprising a C12-C18 fatty acid ester of a hydroxycarboxylic acid and a mono C12-C18 fatty acid ester of glycerol or a mixture comprising a C12-C18 fatty acid ester of a hydroxycarboxylic acid and a mono and di C12-C18 fatty acid ester of glycerol.

In another embodiment the invention relates to a mixture comprising a C12-C18 fatty acid ester of a hydroxycarboxylic acid. Such mixture can be obtained according to the process of the present invention. They can also be obtained by first hydrolyzing the natural oil comprising the glycerides of lower and medium chain fatty acids and thereafter esteryfying the hydrolyzed mixture with a hydroxycarboxylic acid according to standard esterification reactions as described e.g. in U.S. Pat. No. 2,733,252. Such products are particularly useful in the prevention and treatment of anti-microbial infections, both in animals and in human.

In another embodiment the invention relates to a process as described here before for the preparation of a mixture comprising a C12-C16 fatty acid ester of a hydroxycarboxylic acid and a mono C12-C16 fatty acid ester of glycerol or a mixture comprising a C12-C16 fatty acid ester of a hydroxycarboxylic acid and a mono and di C12-C16 fatty acid ester of glycerol.

In another embodiment the invention relates to the mixture comprising a C12-C16 fatty acid ester of a hydroxycarboxylic acid and a mono C12-C16 fatty acid ester of glycerol or a mixture comprising a C12-C16 fatty acid ester of a hydroxycarboxylic acid and a mono and di C12-C16 fatty acid ester of glycerol.

As indicated such mixtures can be obtained according to the process of the present invention including the esterification of natural oils.

The salt of fatty acid ester of hydroxycarboxylic acid admixed with the mono or diglycerides obtained according to the present invention may be optionally purified by washing, recrystallization, distillation, extraction with solution or the like to obtain a product having a higher purity.

In yet another embodiment the invention relates to the use of the product obtained according the process of the present invention for home and personal care applications.

The product prepared according to the disclosure can be used in the prevention and treatment of anti-microbial infections. Thus, in another embodiment the invention relates to products prepared according to the disclosure for use in the prevention and treatment of anti-microbial infections, both in animals and in human.

The products prepared according to the invention are particularly attractive for use against intestinal infections with anaerobic or facultative anaerobic bacteria, even more in particular anaerobic bacteria. The disclosure is of particular interest in the prevention and treatment of intestinal infections by Clostridia. In this respect the product may be administered to animals as a component of a conventional animal feed composition. The product can also be used to improve the fed to gain ratio and to improve digestibility of amino acids administered in animal feeds. To amount to be administered can easily be determined by the man skilled in the art.

In yet another embodiment the invention relates to the fatty acid ester mixture obtainable by the process according to the present disclosure.

In yet another embodiment the invention relates to the mixture comprising a C12-C16 fatty acid ester of a hydroxycarboxylic acid and a mono C12-C16 fatty acid ester of glycerol or a mixture comprising a C12-C16 fatty acid ester of a hydroxycarboxylic acid and a mono and di C12-C16 fatty acid ester of glycerol for use in the prevention and/or treatment of antimicrobial infections.

As indicated herein the triglyceride fatty acid esters in the esterification reaction might be part of natural oils.

The present invention will be elucidated with the following examples, without being limited thereto or thereby.

EXAMPLES

Example 1

Coconut oil (Acros, (10 g; corresponding with 46 mmol of fatty acid chains) was put together with anhydrous sodium lactate (30 g; 267 mmol) and sodium methoxide (0.25 g; 4.6 mmol) in a round bottom flask under inert atmosphere. The reaction mixture was a two-layer system with the coconut oil as a liquid on top of the solid sodium lactate. The mixture was vigorously stirred and heated to 200° C. During heating, at 160° C., the sodium lactate melted and a liquid-liquid two phase system was formed. This system was vigorously stirred. After prolonged stirring and heating, the system changed into a dispersion. The reaction was continued for 8 hours. Characterization by GC revealed C12-1-lactylate formation and C12-monoglyceride formation.

Example 2

Coconut oil (Acros, 78.3 g, corresponding with 357 mmol of fatty acid chains) was put together with anhydrous sodium lactate (41.2 g; 367 mmol) and sodium methoxide (1.0 g; 18.5 mmol) in a round bottom flask under inert atmosphere. The reaction mixture was a two-layer system with the coconut oil as a liquid on top of the solid sodium lactate. The mixture was vigorously stirred and heated to 200° C. During heating, at 150° C., the sodium lactate melted and a liquid-liquid two phase system was formed. This system was vigorously stirred. After prolonged heating and stirring, no lactylate formation was observed on GC. A total of 15 g of C18 lactylate was added to the reaction mixture. After heating and stirring for 5 more hours, C12 lactylate formation was observed on GC.

The invention claimed is:

1. A process for the preparation of a salt of a fatty acid ester of hydroxycarboxylic acid which comprises heating an oil, comprising a mixture consisting essentially of a triglyceride fatty acid ester, a salt of hydroxycarboxylic acid and a catalyst at a temperature at or above the melting temperature of the salt of hydroxycarboxylic acid and subjecting the mixture to ester interchange to form an end product, wherein the removal of an organic solvent is not required during or after completion of the ester interchange, wherein said hydroxycarboxylic acid is a mono- or dicarboxylic acid having 2-6 carbon atoms and 1-3 hydroxyl groups, and wherein the end product does not require removal of an organic solvent.

2. The process according to claim 1 wherein the temperature is kept between 150 and 220° C.

3. The process of claim 2 wherein the temperature is kept between 180 and 200° C.

4. The process of claim 1 wherein said hydroxycarboxylic acid is lactic acid.

5. The process of claim 4 wherein the salt of hydroxycarboxylic acid is sodium lactate.

6. The process of claim 1 wherein said catalyst is alkaline-OR wherein R is H.

7. The process of claim 1 wherein said catalyst is alkaline-OR wherein R is Me.

8. A process according to claim 1 wherein the natural oil is coconut oil.

9. A process according to claim 1 wherein the natural oil is palm kernel oil.

10. The process of claim 1 wherein the molar ratio of salt of hydroxycarboxylic acid to the triglyceride fatty acid ester is from 10:1 to −0.5:1.

11. The process according to claim 1 and further comprising adding a surfactant to the mixture during the ester interchange.

12. The process according to claim 11 wherein the surfactant is added in an amount ranging from 0-20% on a mass basis as compared to the starting materials.

13. A process according to claim 1 wherein in addition to the salt of a fatty acid ester of hydroxycarboxylic acid, mono- and di-fatty acid esters of glycerol are produced.

14. The process according to claim 1, wherein the process is carried out under inert atmosphere.

15. The process according to claim 1, wherein the molar ratio of the salt of the hydroxycarboxylic acid to the triglyceride fatty acid ester is from 25:1 to 0.5:1.

16. The process according to claim 1 were in the triglyceride fatty acid ester comprises C12 to C16 fatty acid chains.

17. The process according to claim 1 wherein the natural oil is a mixture of coconut oil and palm kernel oil.

18. The process according to claim 1 wherein the ester interchange is completed without using an organic solvent.

19. The process according to claim 1, and further comprising adding a surfactant to the mixture.

* * * * *